United States Patent
Nguyen et al.

(10) Patent No.: US 9,084,874 B2
(45) Date of Patent: Jul. 21, 2015

(54) METHOD AND SYSTEM TO MAINTAIN A FIXED DISTANCE DURING COATING OF A MEDICAL DEVICE

(75) Inventors: Binh Nguyen, Newark, CA (US); Benjamyn Serna, Gilroy, CA (US); Stephen D. Pacetti, San Jose, CA (US); Victoria M. Gong, Sunnyvale, CA (US)

(73) Assignee: ABBOTT LABORATORIES, Santa Clara, CA (US)

( * ) Notice: Subject to any disclaimer, the term of this patent is extended or adjusted under 35 U.S.C. 154(b) by 855 days.

(21) Appl. No.: 13/158,131

(22) Filed: Jun. 10, 2011

(65) Prior Publication Data
US 2012/0315376 A1    Dec. 13, 2012

(51) Int. Cl.
| | |
|---|---|
| B05C 5/02 | (2006.01) |
| B05B 13/04 | (2006.01) |
| B05C 13/02 | (2006.01) |
| A61M 25/10 | (2013.01) |

(52) U.S. Cl.
CPC ........ *A61M 25/1029* (2013.01); *B05B 13/0442* (2013.01); *B05C 5/02* (2013.01); *A61M 2025/105* (2013.01); *A61M 2025/1031* (2013.01)

(58) Field of Classification Search
CPC ............................. B05C 5/02; B05B 13/0442
See application file for complete search history.

(56) References Cited

U.S. PATENT DOCUMENTS

| | | | |
|---|---|---|---|
| 4,743,465 A * | 5/1988 | Saeki et al. ................... | 427/97.3 |
| 4,748,982 A | 6/1988 | Horzewski et al. | |
| 5,300,085 A | 4/1994 | Yock | |
| 5,370,614 A | 12/1994 | Amundson et al. | |
| 5,464,650 A | 11/1995 | Berg et al. | |
| 5,496,346 A | 3/1996 | Horzewski et al. | |
| 5,591,227 A | 1/1997 | Dinh et al. | |
| 5,626,600 A | 5/1997 | Horzewski et al. | |
| 5,649,977 A | 7/1997 | Campbell | |
| 5,911,452 A | 6/1999 | Yan | |
| 5,980,972 A | 11/1999 | Ding | |
| 6,120,847 A | 9/2000 | Yang et al. | |
| 6,406,457 B1 | 6/2002 | Wang et al. | |
| 6,478,807 B1 | 11/2002 | Foreman et al. | |
| 6,494,906 B1 | 12/2002 | Owens | |
| 6,669,980 B2 | 12/2003 | Hansen | |
| 6,676,987 B2 | 1/2004 | Zhong et al. | |
| 6,743,462 B1 * | 6/2004 | Pacetti ......................... | 427/2.24 |
| 7,241,344 B2 | 7/2007 | Worsham et al. | |
| 7,335,227 B2 | 2/2008 | Jalisi | |
| 7,378,105 B2 | 5/2008 | Burke et al. | |

(Continued)

OTHER PUBLICATIONS

U.S. Appl. No. 12/882,990, filed Sep. 15, 2010.

(Continued)

*Primary Examiner* — Dah-Wei D Yuan
*Assistant Examiner* — Stephen Kitt
(74) *Attorney, Agent, or Firm* — Baker Botts L.L.P.

(57) ABSTRACT

Method and system to coat an expandable member of a medical device comprising a support structure to support the expandable member and an applicator positioned with at least one outlet proximate a surface of an expandable member. A drive assembly establishes relative movement between the at least one outlet and the surface of the expandable member to apply fluid on the surface of the expandable member along a coating path. A tracking mechanism maintains a substantially fixed distance between the at least one outlet and the surface of the expandable member during relative movement therebetween by displacing the at least one outlet relative to the expandable member.

16 Claims, 7 Drawing Sheets

(56) References Cited

U.S. PATENT DOCUMENTS

| | | | |
|---|---|---|---|
| 7,445,792 | B2 | 11/2008 | Toner et al. |
| 7,455,876 | B2 | 11/2008 | Castro et al. |
| 7,504,125 | B1 | 3/2009 | Pacetti et al. |
| 7,524,527 | B2 | 4/2009 | Stenzel |
| 2001/0021419 | A1* | 9/2001 | Luthje et al. .................. 427/421 |
| 2004/0062875 | A1* | 4/2004 | Chappa et al. ................. 427/421 |
| 2004/0073284 | A1 | 4/2004 | Bates et al. |
| 2004/0234748 | A1 | 11/2004 | Stenzel |
| 2005/0196518 | A1 | 9/2005 | Stenzel |
| 2007/0031611 | A1 | 2/2007 | Babaev |
| 2007/0088255 | A1 | 4/2007 | Toner et al. |
| 2007/0179591 | A1 | 8/2007 | Baker et al. |
| 2008/0113081 | A1 | 5/2008 | Hossainy et al. |
| 2009/0226598 | A1 | 9/2009 | Feng et al. |
| 2010/0023108 | A1 | 1/2010 | Toner et al. |
| 2010/0030183 | A1 | 2/2010 | Toner et al. |
| 2010/0040766 | A1* | 2/2010 | Chappa et al. ................. 118/320 |
| 2010/0055294 | A1 | 3/2010 | Wang et al. |
| 2011/0151199 | A1* | 6/2011 | Nelson et al. .................. 428/174 |
| 2011/0281019 | A1 | 11/2011 | Gong et al. |
| 2011/0281020 | A1* | 11/2011 | Gong et al. ..................... 427/2.1 |
| 2012/0022540 | A1 | 1/2012 | Chasmawala et al. |
| 2012/0064223 | A1 | 3/2012 | Gamez et al. |
| 2012/0065583 | A1 | 3/2012 | Serna et al. |
| 2012/0128863 | A1 | 5/2012 | Nguyen et al. |
| 2012/0143054 | A1 | 6/2012 | Eaton et al. |
| 2012/0315374 | A1 | 12/2012 | Nguyen et al. |
| 2012/0315375 | A1* | 12/2012 | Shen et al. .................... 427/2.28 |
| 2014/0113059 | A1 | 4/2014 | Shen et al. |

OTHER PUBLICATIONS

U.S. Appl. No. 13/158,057, filed Jun. 10, 2011.
U.S. Appl. No. 13/158,101, filed Jun. 10, 2011.
Unverdoben, Martin, "The Paclitaxel-Eluting PTCA-Balloon Catheter in Coronary Artery Disease PEPCAD I-SVD PEPCAD II-ISR",Clinical Research Institute, Center for Cardiovascular Diseases, 2005-2006, Rotenburg/Fulda, Germany.
U.S. Appl. No. 13/109,156, filed May 17, 2011.
U.S. Appl. No. 12/882,990, filed Apr. 8, 2013, Response to Non-Final Office Action.
U.S. Appl. No. 13/108,283, filed Mar. 28, 2013, Non-Final Office Action.
U.S. Appl. No. 13/280,067, filed Apr. 26, 2013, Applicant Summary of Interview with Examiner.
U.S. Appl. No. 12/882,953, filed Apr. 12, 2013, Response to Non-Final Office Action.
U.S. Appl. No. 13/158,101, filed Apr. 26, 2013, Restriction Requirement.
U.S. Appl. No. 13/109,156, filed Apr. 26, 2013, Restriction Requirement.
U.S. Appl. No. 13/158,057, filed Apr. 26, 2013, Restriction Requirement.
U.S. Appl. No. 14/078,212, filed Nov. 12, 2013.
U.S. Appl. No. 12/882,953, filed Dec. 9, 2013, Notice of Allowance.
U.S. Appl. No. 12/882,953, filed Nov. 15, 2013, Request for Continued Examination (RCE).
U.S. Appl. No. 12/882,953, filed Oct. 28, 2013, Advisory Action.
U.S. Appl. No. 12/882,953, filed Oct. 16, 2013, Response to Final Office Action.
U.S. Appl. No. 13/109,156, filed Oct. 25, 2013, Applicant Initiated Interview Summary.
U.S. Appl. No. 13/158,057, filed Oct. 24, 2013, Applicant Initiated Interview Summary.
U.S. Appl. No. 12/882,990, filed Dec. 2, 2013, Amendment and Request for Continued Examination (RCE).
U.S. Appl. No. 12/882,990, filed Oct. 11, 2013, Advisory Action.
U.S. Appl. No. 12/882,990, filed Oct. 1, 2013, Response to Final Office Action.
U.S. Appl. No. 13/108,283, filed Nov. 12, 2013, Issue Fee payment.
U.S. Appl. No. 13/158,101, filed Oct. 7, 2013, Notice of Allowance.
U.S. Appl. No. 13/109,156, filed Sep. 10, 2013, Non-Final Office Action.
U.S. Appl. No. 12/882,953, filed Aug. 16, 2013, Final Office Action.
U.S. Appl. No. 13/158,057, filed Sep. 12, 2013, Non-Final Office Action.
U.S. Appl. No. 12/882,990, filed Aug. 1, 2013, Final Office Action.
U.S. Appl. No. 13/108,283, filed Aug. 12, 2013, Notice of Allowance.
PlumbingSupply.com, "Pipe Hangers and Brackets", (2/2001), www.plumbingsupply.com/pipehangers.htlm.
Vivekanandhan, et al., "Computer-Aided Torch Trajectory Generation for Automated Coating of Parts with Complex Surfaces", *Journal of Thermal Spray Technology*. 3(2):208-215 (1994).
Cornell, Maintaining Distance Using Sonar video, Youtube (2010) http://www.youtube.com/watch?v=Pj6Jxo2Sqgw, [Downloaded on Sep. 16, 2013].
U.S. Appl. No. 12/882,953, filed Sep. 15, 2010.
U.S. Appl. No. 13/280,067, filed Oct. 24, 2011.
U.S. Appl. No. 13/108,283, filed May 16, 2011.
U.S. Appl. No. 12/882,953, filed Jan. 15, 2013, Non-Final Office Action.
U.S. Appl. No. 12/882,990, filed Dec. 6, 2012, Non-Final Office Action.
U.S. Appl. No. 14/146,148, filed Jan. 2, 2014.
U.S. Appl. No. 14/078,212, filed Jun. 6, 2014, Non-Final Office Action.
U.S. Appl. No. 12/882,953, filed Mar. 7, 2014, Issue Fee payment.
U.S. Appl. No. 12/882,990, filed Dec. 19, 2013, Non-Final Office Action.
U.S. Appl. No. 13/109,156, filed Mar. 20, 2014, Response to Final Office Action.

\* cited by examiner

METHOD AND SYSTEM TO MAINTAIN A FIXED DISTANCE DURING COATING OF A MEDICAL DEVICE

BACKGROUND OF THE DISCLOSED SUBJECT MATTER

1. Field of the Disclosed Subject Matter

The presently disclosed subject matter is related to the delivery of a therapeutic agent from an interventional medical device. Particularly, the disclosed subject matter relates to the method and system for maintaining a fixed distance between an outlet of an applicator and the surface of an expandable member during application of one or more therapeutic agents.

2. Description of Related Subject Matter

Atherosclerosis is a disease affecting arterial blood vessels. It is characterized by a chronic inflammatory response in the walls of arteries, which is in large part due to the accumulation of lipid, macrophages, foam cells and the formation of plaque in the arterial wall. Atherosclerosis is commonly referred to as hardening of the arteries, although the pathophysiology of the disease manifests itself with several different types of lesions ranging from fibrotic to lipid laden to calcific. Angioplasty is a vascular interventional technique involving mechanically widening an obstructed blood vessel, typically caused by atherosclerosis.

During angioplasty, a catheter having a folded balloon is inserted into the vasculature of the patient and is passed to the narrowed location of the blood vessel at which point the balloon is inflated to the desired size by fluid pressure. Percutaneous coronary intervention (PCI), commonly known as coronary angioplasty, is a therapeutic procedure to treat the stenotic regions in the coronary arteries of the heart, often found in coronary heart disease. In contrast, peripheral angioplasty, commonly known as percutaneous transluminal angioplasty (PTA), generally refers to the use of mechanical widening of blood vessels other than the coronary arteries. PTA is most commonly used to treat narrowing of the leg arteries, especially, the iliac, external iliac, superficial femoral and popliteal arteries. PTA can also treat narrowing of carotid and renal arteries, veins, and other blood vessels.

Although the blood vessel is often successfully widened by angioplasty, sometimes the treated region of the blood vessel undergoes vasospasm, or abrupt closure after balloon inflation or dilatation, causing the blood vessel to collapse after the balloon is deflated or shortly thereafter. One solution to such collapse is stenting the blood vessel to prevent collapse. A stent is a device, typically a metal tube or scaffold that is inserted into the blood vessel after, or concurrently with angioplasty, to hold the blood vessel open.

While the advent of stents eliminated many of the complications of abrupt vessel closure after angioplasty procedures, within about six months of stenting a re-narrowing of the blood vessel can form, a condition known as restenosis. Restenosis was discovered to be a response to the injury of the angioplasty procedure and is characterized by a growth of smooth muscle cells and extracellular matrix—analogous to a scar forming over an injury. To address this condition, drug eluting stents were developed to reduce the reoccurrence of blood vessel narrowing after stent implantation. A drug eluting stent is a stent that has been coated with a drug, often in a polymeric carrier, that is known to interfere with the process of re-narrowing of the blood vessel (restenosis). Examples of various known drug eluting stents are disclosed in U.S. Pat. Nos. 5,649,977; 5,464,650; 5,591,227; 7,378,105; 7,445,792; and 7,335,227, each of which are hereby incorporated by reference in their entirety. However, a drawback of drug eluting stents is a condition known as late stent thrombosis. This is an event where a blood clot forms inside the stent, which can occlude blood flow.

Drug coated balloons are believed to be a viable alternative to drug eluting stents in the treatment of atherosclerotic lesions. In a study which evaluated restenosis, and the rate of major adverse cardiac events such as heart attack, bypass, repeat stenosis, or death in patients treated with drug coated balloons and drug eluting stents, the patients treated with drug coated balloons experienced only 3.7% restenosis and 4.8% MACE (major adverse coronary events) as compared to patients treated with drug eluting stents, in which restenosis was 20.8% and 22.0% MACE rate. (See, PEPCAD II study, Rotenburg, Germany)

However, drug coated balloons present certain unique challenges. For example, the drug carried by the balloon needs to remain on the balloon during delivery to the lesion site, and released from the balloon surface to the blood vessel wall when the balloon is expanded inside the blood vessel. For coronary procedures, the balloon is typically inflated for less than one minute, typically about thirty seconds. The balloon inflation time may be longer for a peripheral procedure, however typically even for peripheral procedures the balloon is expanded for less than 5 minutes. Due to the short duration of contact between the drug coated balloon surface and the blood vessel wall, the balloon coating must exhibit efficient therapeutic agent transfer and/or efficient drug release during inflation. Thus, there are challenges specific to drug delivery via a drug coated or drug eluting balloon that are not present with a drug eluting stent.

Furthermore, conventional techniques for applying a coating, such as a therapeutic agent, may not be desirable for coating balloons, or other expandable members of medical devices. Such conventional techniques include spraying (air-atomization, ultrasonic, electrostatic, etc.), dip-coating, spin-coating, vapor deposition, roll coating, micro-droplet coating, etc. However, it is desirable to control the amount or dosage of therapeutic agent applied to the surface of the expandable member, and the location in which the therapeutic agent is applied. Many conventional techniques do not provide sufficient control over dosage, coating uniformity or edge control. Such control is further compromised when coating a medical device having a non-uniform configuration, such as a tapered balloon or a partially-inflated balloon, or when coating a medical device having a non-symmetrical surface, such as a balloon having a warped or bowed configuration. For example, peripheral balloons, being longer than coronary balloons, are more susceptible to warping or bowing along the longitudinal axis when inflated. Consequently, the amount and uniformity of coating applied to the balloon surface using conventional techniques may be compromised due to the non-uniform shape of the expandable member.

Thus, there remains a need for, and an aim of the disclosed subject matter is directed toward, maintaining a fixed distance between the coating applicator and the surface of the expandable member during the application of one or more therapeutic agents thereto.

SUMMARY OF THE DISCLOSED SUBJECT MATTER

The purpose and advantages of the disclosed subject matter will be set forth in and are apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a method and system of coating an expandable member of a medical device. The method of coating an expandable member of a medical device includes providing an applicator in fluid communication with a fluid source, with the applicator having at least one outlet for applying fluid therefrom, and positioning the applicator proximate a surface of an expandable member, which is supported along a longitudinal axis. Relative movement is established between the at least one outlet and the surface of the expandable member along a coating path while maintaining a substantially fixed distance between the at least one outlet and the surface of the expandable member during relative movement therebetween. Maintaining the substantially fixed distance includes displacing the at least one outlet to track the surface of the expandable member. Fluid is applied from the at least one outlet to form a controlled coating of fluid on the surface of the expandable member along the coating path. The substantially fixed distance between the expandable member and the at least one outlet is maintained by displacing the outlet to track the surface of the expandable member. The substantially fixed distance includes tracking the surface of expandable member using a tracking mechanism, and displacing the at least one outlet in response to the tracking mechanism. The relative movement includes rotation, translation, or a combination thereof, of at least one of the expandable member and the at least one outlet. In one embodiment, the expandable is rotated relative to the at least one outlet at a speed of between about 5 rpm and about 1000 rpm. In another embodiment, the expandable member is translated relative to the at least one outlet at a speed of between about 0.02 cm/sec and about 10 cm/sec.

The disclosed subject matter also provides a system for coating an expandable member of a medical device. The system includes a support structure to support an expandable member of a medical device along a longitudinal axis, an applicator in fluid communication with a fluid source, a drive assembly to establish relative movement between the outlet and the surface of the expandable member to apply fluid on the surface of the expandable member along a coating path, and a tracking mechanism to maintain a substantially fixed distance between the outlet and the surface of the expandable member during relative movement therebetween. The applicator has at least one outlet for applying fluid of the fluid source therefrom, and is positioned with the outlet proximate a surface of an expandable member supported by the support structure. Maintaining the substantially fixed distance includes displacing the outlet in response to the tracking mechanism to track the surface of the expandable member. In one embodiment, the applicator includes a flexible connection between the outlet and the fluid source. In one embodiment, the substantially fixed distance is less than about 40 times a cross dimension of the outlet.

In accordance with the disclosed subject matter, the tracking mechanism can include a stylus for discrete contact with the surface of the expandable member or a frame to substantially surround the expandable member. In one embodiment, the stylus is disposed proximate the outlet at an upstream location along the coating path. In one embodiment, the tracking mechanism includes a shuttle mechanism for displacement of the frame. In one embodiment, the shuttle mechanism is a micro XY stage. The outlet can be configured to pivot about a hinge axis, or for displacement in at least one direction in a plane orthogonal to the longitudinal axis. In accordance with another embodiment, the outlet is configured for displacement along at least a first axis and a second axis in the plane. In one embodiment, the outlet is rigidly coupled to the tracking mechanism. In one embodiment, the method further includes at least partially expanding the expandable member prior to dispensing fluid to the surface of the expandable member.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

DETAILED DESCRIPTION OF THE PREFERRED EMBODIMENT

Reference will now be made in detail to the preferred embodiments of the disclosed subject matter, an example of which is illustrated in the accompanying drawings. The method and corresponding steps of the disclosed subject matter will be described in conjunction with the detailed description of the system.

The methods and systems presented herein can be used for applying one or more coatings to a medical device. The disclosed subject matter is particularly suited for applying a uniform coating of therapeutic agents, and other fluid compounds, to select portions of an expandable member. While the disclosed subject matter references application of a fluid to an expandable member, it is to be understood that a variety of coatings including polymeric, therapeutic, or matrix coatings, can be applied to various surfaces of medical devices, as so desired.

The disclosed subject matter provides a method, and corresponding system, to coat an expandable member, or select portions thereof, by a variety of application processes while maintaining a substantially fixed distance between the outlet of the applicator and the surface of the expandable member.

The disclosed subject matter provides a system and corresponding method of coating an expandable member of a medical device, which comprises providing an applicator in fluid communication with a fluid source, with the applicator having at least one outlet for applying fluid therefrom, and positioning the applicator proximate a surface of an expandable member. Relative movement is established between the at least one outlet and the surface of the expandable member along a coating path while maintaining a substantially fixed distance between the at least one outlet and the surface of the expandable member during relative movement therebetween, wherein maintaining the substantially fixed distance includes displacing the at least one outlet to track the surface of the expandable member. From the fixed distance, fluid is applied from the at least one outlet to form a coating of fluid on the surface of the expandable member along the coating path.

Figure 1:
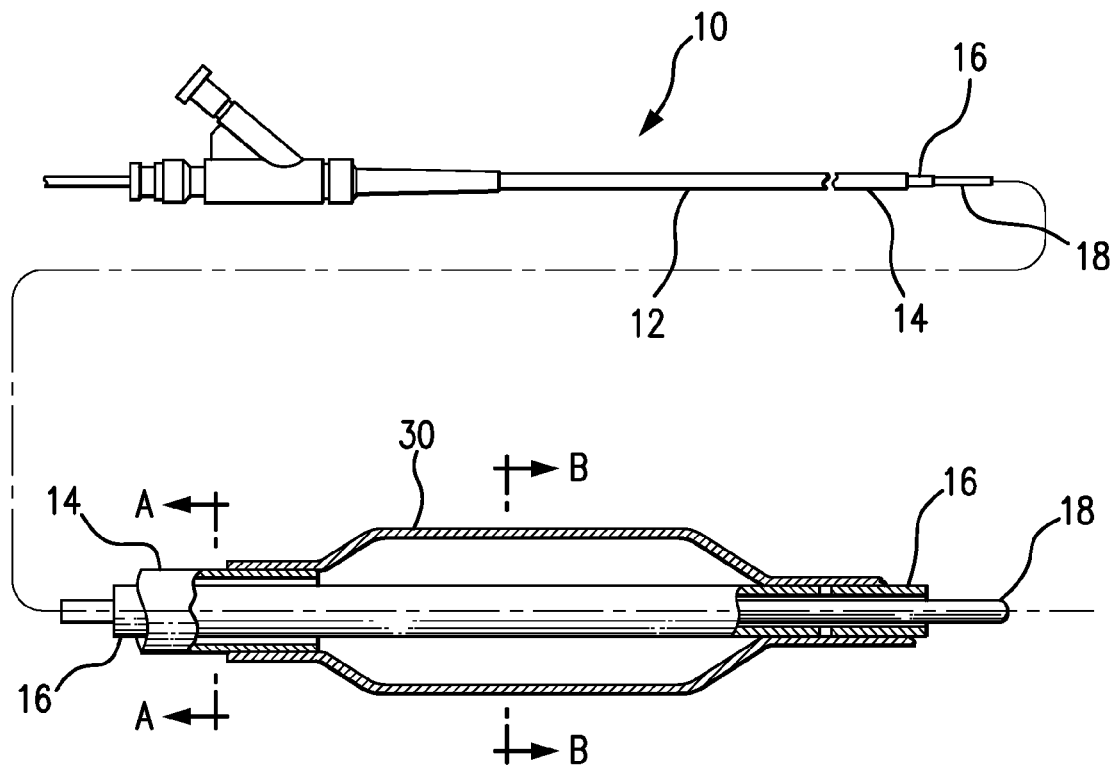
FIG. 1 is a schematic side view in partial cross-section of a representative balloon catheter in accordance with the disclosed subject matter.
Figure 1A:
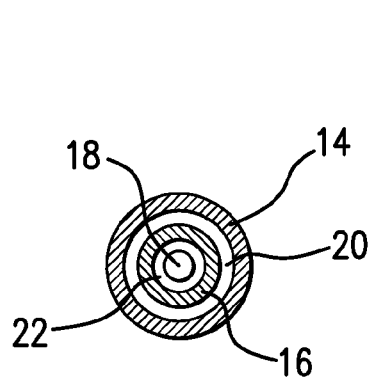
FIG. 1A is a cross-sectional view taken along lines A-A in FIG. 1.

For purpose of explanation and illustration, and not limitation, an exemplary embodiment of a medical device having an expandable member is shown schematically in FIGS. 1 and 1A. Particularly, and as illustrated, the medical device embodied herein is a balloon catheter 10, which includes an elongated catheter shaft 12 having a proximal end and having a distal end and an expandable member 30 located proximate the distal end of the catheter shaft. The expandable member, or balloon as depicted herein for purpose of illustration and not limitation, has an outer surface and an inner surface disposed at the distal end portion of the catheter shaft. In accordance with the disclosed subject matter, a coating is applied to at least a portion of the outer surface of the balloon.

Figure 1B:
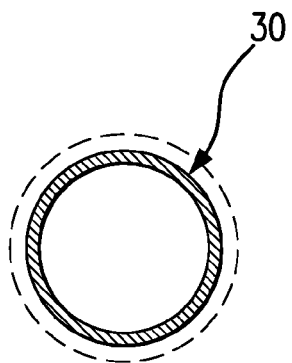
FIG. 1B is a cross-sectional view taken along lines B-B in FIG. 1.

The elongated catheter shaft 12 comprises an outer tubular member 14 and an inner tubular member 16. The outer tubular member 14 defines an inflation lumen 20 disposed between the proximal end portion and the distal end portion of the catheter shaft 12. Specifically, as illustrated in FIG. 1A, the coaxial relationship of this representative embodiment defines an annular inflation lumen 20 between the inner tubular member 16 and the outer tubular member 14. The expandable member 30 is in fluid communication with the inflation lumen 20. The inflation lumen can supply an inflation medium under positive pressure and can withdraw the inflation medium, i.e. provide negative pressure, from the expandable member. The expandable member 30 can thus be inflated and deflated. The elongated catheter is sized and configured for delivery through a tortuous anatomy, and can further include a guidewire lumen 22 that permits it to be delivered over a guidewire 18. As illustrated in FIG. 1A, the inner tubular member 16 defines the guidewire lumen 22 for the guidewire 18. Although FIGS. 1 and 1b illustrate the guidewire lumen formed as a separate inner member having an over-the-wire (OTW) construction, the guidewire lumen can be formed of a dual lumen member with either an over-the wire (OTW) or a rapid-exchange (RX) construction, as is well known in the art.

A wide variety of balloon catheters and expandable members constructions are known and suitable for use in accordance with the disclosed subject matter. For example, the expandable member can be made from polymeric material such as compliant, non-compliant or semi-compliant polymeric material or polymeric blends. Examples of such suitable materials include, but are not limited to, nylon 12, nylon 11, nylon 9, nylon 6, nylon 6/12, nylon 6/11, nylon 6/9, and nylon 6/6, polyurethane, silicone-polyurethane, polyesters, polyester copolymers, and polyethylene. Examples of other balloon and catheter embodiments which can be employed in accordance with the disclosed subject matter include U.S. Pat. Nos. 4,748,982; 5,496,346; 5,626,600; 5,300,085; and 6,406,457 and Application patent application Ser. Nos. 12/371,426; 11/539,944; and 12/371,422, each of which are hereby incorporated by reference in their entirety.

In a preferred embodiment, the coating is applied to the expandable member of the fully assembled medical device. As described above with reference to FIGS. 1A-B, medical devices such as the catheter 10 include a plurality of components which are typically manufactured as separate discrete components and thereafter assembled together. Applying a coating to the expandable member at an upstream stage of an assembly line can require extensive measures to minimize or prevent the coating from being exposed to various equipment and processes during the downstream stages of the assembly line. Such exposure can render the coating prone to damage and/or contamination during final assembly of the catheter, and can result in scrapping of the entire catheter. Similarly, coating of the expandable member prior to assembly of the catheter can result in contamination of equipment in the assembly line if appropriate measures are not taken. In order to avoid such damage and exposure in conventional catheter assembly lines, additional equipment including monitoring and safety controls would be required. Accordingly, applying the coating to the expandable member after assembly of the catheter, as disclosed herein, avoids the unnecessary complexity and excessive costs associated with a modified assembly line.

In accordance with the disclosed subject matter, any of a variety of fluid compositions can be applied to the expandable member. For example, the fluid can include a therapeutic agent for treatment of a disease state. Examples of suitable therapeutic agents include anti-proliferative, anti-inflammatory, antineoplastic, antiplatelet, anti-coagulant, anti-fibrin, antithrombotic, antimitotic, antibiotic, antiallergic and antioxidant compounds. Such therapeutic agents can be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, and a retroviral vector. As embodied herein, for purpose of illustration and not limitation, the therapeutic agents include a cytostatic drug. The term "cytostatic" as used herein means a drug that mitigates cell proliferation but allows cell migration. These cytostatic drugs, include for the purpose of illustration and without limitation, macrolide antibiotics, rapamycin, everolimus, zotarolimus, biolimus, temsirolimus, deforolimus, novolimus, myolimus, structural derivatives and functional analogues of rapamycin, structural derivatives and functional analogues of everolimus, structural derivatives and functional analogues of zotarolimus and any marcrolide immunosuppressive drugs. The term "cytotoxic" as used herein means a drug used to inhibit cell growth, such as chemotherapeutic drugs. Some non-limiting examples of cytotoxic drugs include vincristine, actinomycin, cisplatin, taxanes, paclitaxel, and protaxel.

Additionally or alternatively, the fluid can include other compounds or additives, such as polymers, binding agents, plasticizers, solvents, surfactants, additives, chelators, fillers, and the like. An exemplary formulation according to the disclosed subject matter includes zotarolimus, polyvinylpyrrolidone and glycerol. In one embodiment, the therapeutic agent can be provided in liquid form or dissolved in a suitable solvent. In one embodiment, the solvent is acetone. In another embodiment, the therapeutic agent is provided as a particulate and mixed in a suitable carrier for application as a fluid.

In accordance with an aspect of the disclosed subject matter, a variety of techniques for applying a coating of therapeutic agent can be employed, such as spraying (air-atomization, ultrasonic, electrostatic, etc.), vapor deposition, microdroplet coating, etc. Additionally or alternatively, a direct coating process can be used and is embodied herein, as further disclosed in U.S. Pat. No. 7,455,876 and U.S. Patent Publication No. 2010/0055294, the entirety of each is hereby incorporated by reference, can be employed in accordance with the disclosed subject matter. For purpose of illustration and not limitation, reference will be made to a direct coating process, although the disclosed subject matter is equally applicable to other suitable coating application techniques.

Figure 2:
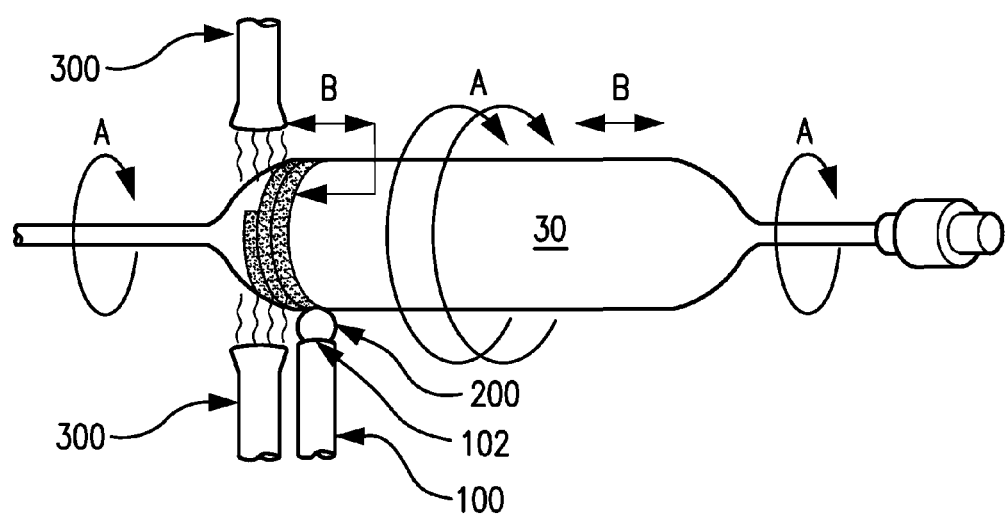
FIG. 2 is a schematic view of an applicator assembly for direct fluid coating on the surface of an expandable member.

An exemplary embodiment of the direct coating process and system is illustrated in FIG. 2 for purpose of explanation and not limitation. The applicator depicted herein is shown as a pipette 100 having an outlet positioned proximate expandable member 30 such that the fluid dispensed from the pipette is deposited on the surface of the expandable member. FIG. 2 depicts the pipette 100 generally normal to or at a right angle to the balloon surface. However, alternative alignments and orientations can be used as desired or needed for the type and dimensions of expandable members.

Coating process and systems of the disclosed subject matter can be performed with the expandable member in a partially or fully inflated condition, or in a deflated condition if desired. If deflated, the expandable member can have a generally smooth exposed surface if made of a compliant material, or can be pleated, folded, wrinkled or pressed if made of a semi-compliant or non-compliant material. For purpose of illustration, FIG. 2 shows the expandable member 30 in an inflated condition to allow coating of all or select portions of the outer surface. Additionally, the temperature of the expansion medium, or the expandable member itself, can be controlled to further maintain or define the contour of the expandable member.

As fluid is delivered from the applicator 100, relative movement is established between the applicator 100 and the expandable member 30 to affect a continuous or patterned coating path as desired. For example, and as depicted in FIG. 2, the coating path can define a generally continuous spiral or helical pattern along the outer surface of the expandable member. Alternatively, coating paths can be established as discrete circumferential rings, discrete lines extending along the expandable members longitudinal axis, or combinations or portions thereof.

The relative movement can include rotation, translation, or combinations thereof, of either, or both, the expandable member and the applicator. For example, the expandable member 30 can be rotated about its central axis, as shown by arrows A in FIG. 2, and simultaneously translated along the central axis, as shown by arrow B in FIG. 2. Additionally, or alternatively the expandable member 30 can rotate relative a first axis, and the applicator 100 translate relative the axis, e.g., to define a helical coating path. Accordingly, any number of coating paths can be selected and provided on the expandable member. The various movements described herein can be performed simultaneously, sequentially, continuously or intermittently, as so desired. As embodied herein, the expandable member can be rotated at a speed of between about 5 and 1000 rpm, depending upon the coating fluid and related parameters during coating, and translated relative to the applicator at a speed of between about 0.02 and 10 cm/sec.

The desired portions or areas of the expandable member can be coated with a single pass or cycle of relative movement between the expandable member and applicator. Alternatively, a plurality of passes or cycles of coating operation can be performed. Such multiple passes or cycles allow for further variation in the coating properties along the expandable member length or select areas. For example, one portion of the expandable member can be coated with a different number of coating layers of fluid than another portion of the expandable member thereby creating a gradient of the coating on the expandable member. Further, various layers of different coating formulations can be applied to the expandable member using the method and system disclosed herein. For example, one or more layers of therapeutic-free primers, concentrated therapeutic layers, drug-excipient layers, and/or release control layers can be applied. These varied coating properties allow for greater flexibility and customization of the catheter to provide a greater range of applications and uses.

In accordance with another aspect of the disclosed subject matter, drying can be employed to accelerate the coating process, such as by applying heat, forced gas, cooled gas, vacuum, infra-red energy, microwave energy, or a combination thereof to the coated surface of the expandable member. With regard to a direct coating operation, for purpose of illustration and not limitation, FIG. 2 shows a dryer 300 can be provided upstream of or adjacent to the applicator for drying concurrent with or shortly after coating application. In one embodiment, the drying nozzle can be collinear with the applicator by circumscribing or surrounding the applicator with an annular opening. Additionally or alternatively, drying can be conducted between successive coating passes or cycles. The dryer 300 can be oriented at any suitable angle relative to the surface of the expandable member, and can be configured for relative movement with or independent of the applicator relative to the expandable member.

While the direct coating applicator of the embodiment illustrated in FIG. 2 is depicted as a pipette, additional or alternative applicators can be employed. Some examples of suitable direct coating applicators include flexible tubing, coaxial tubing, hypotubes, dies, ball-bearing dispense tubing, syringe, needles, brushes, sponges, cones and foam applicators. Furthermore, FIG. 2 depicts a direct coating applicator having a single outlet 102, a plurality of outlets can be employed if desired. The outlets can be disposed adjacent each other along the axis of the expandable member, and/or spaced circumferentially about the expandable member. In this regard, one or more of a plurality of reservoirs containing the same or different coating solutions can be provided in fluid communication with each outlet of the applicator, respectively. As with the outlet of FIG. 2, each applicator outlet can be positioned at various locations and orientations relative to the surface of the expandable member. Additionally, the expandable member 30 can be oriented in a generally horizontal position, as shown in FIG. 2, vertically, or at or at any angle between as suitable. For example, arranging the expandable member in a vertical configuration can be advantageous for larger size expandable members, e.g., peripheral balloons, to allow gravitational force to act parallel with the longitudinal axis of the expandable member to reduce deformation of the expandable member and associated catheter shaft.

Movement of the medical device and/or the outlet of the applicator is accomplished by providing a support assembly or a support structure. The support assembly or support structure can maintain the position of one element, e.g., the applicator, while allowing movement of the other element, e.g., the medical device. Alternatively, the support assembly or support structure can allow movement of both elements. Movement can be performed manually, or by providing a drive assembly with suitable drive source, such as a motor or the like, and appropriate controller as know in the art.

In accordance with the disclosed subject matter, the applicator is maintained at a predetermined or fixed distance from the expandable member surface. Maintaining a fixed distance between the applicator outlet and the expandable member, in combination with rotation and translation as discussed above, provides greater control over the coating pattern to be applied to the expandable member surface. Such control provides a consistent and uniform dosage of the therapeutic agent along the surface of the expandable member, resulting in a coating with increased efficacy and content uniformity. Additionally, maintaining a fixed distance allows greater control for coating an expandable member at discrete locations, if desired, or with non-uniform patterns, such as to create varied local areal density along selected portions of the expandable member.

Furthermore, maintaining a fixed distance between the applicator outlet and the expandable member surface reduces the amount of waste or excess coating which is not retained on the expandable member. For example, with spray coating techniques, the amount of waste or excess coating generally increases with the distance between the outlet(s) and the surface of the expandable member. Conversely, if the distance between the applicator outlet and the expandable member surface are too small, undesired or accidental contact between the applicator outlet and expandable member surface can occur resulting in tearing or scratching of the expandable member surface, abrasion to the coating applied to the expandable member, or bare spots in the coating. The preferred distance between the outlet and the surface of the expandable member can depend upon a number of variables, including viscosity of the fluid, surface tension of the fluid, pump rate of the fluid, diameter of the applicator exit orifice, volatility of the solvents in the fluid, speed at which the fluid is dispensed, diameter or shape of the expandable member, and/or size of the outlet opening. For example, when using a pipette type applicator for direct coating applications, the distance between the outlet and the surface generally should be less than about 40 times the smallest cross dimension of the outlet.

As disclosed herein, the fixed distance between the outlet and the surface of the expandable member is maintained by displacing the outlet to track the surface of the expandable member. Such a technique is generally suitable for any of a variety of known expandable members, including conventional cylindrical balloons, as well as tapered, shaped and stepped balloons or the like. Also, by tracking the surface of the expandable member, the various coating techniques can adjust for minor distortions or features—whether intentional or unintentional—in the surface of the expandable member. Furthermore, and as described further below, the method and system of the disclosed subject matter also is suitable for use with bowed or warped balloons, such as peripheral balloons that due to their longer lengths can have greater distortions.

Figure 3:
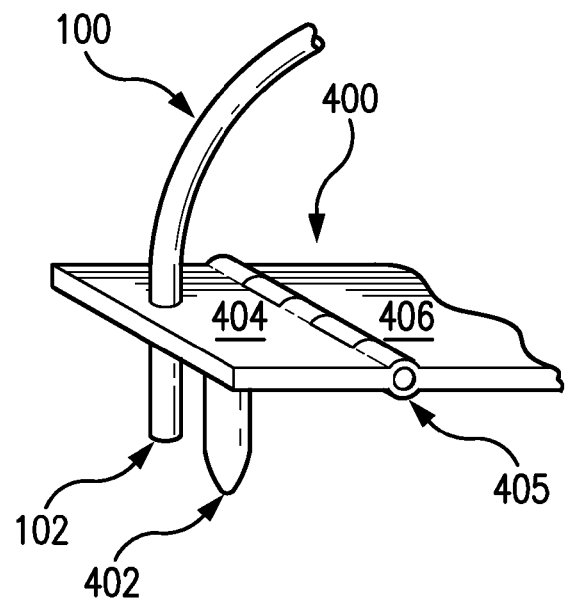
FIG. 3 is a schematic detail view of a tracking mechanism for an applicator outlet in accordance with the disclosed subject matter.
Figure 4:
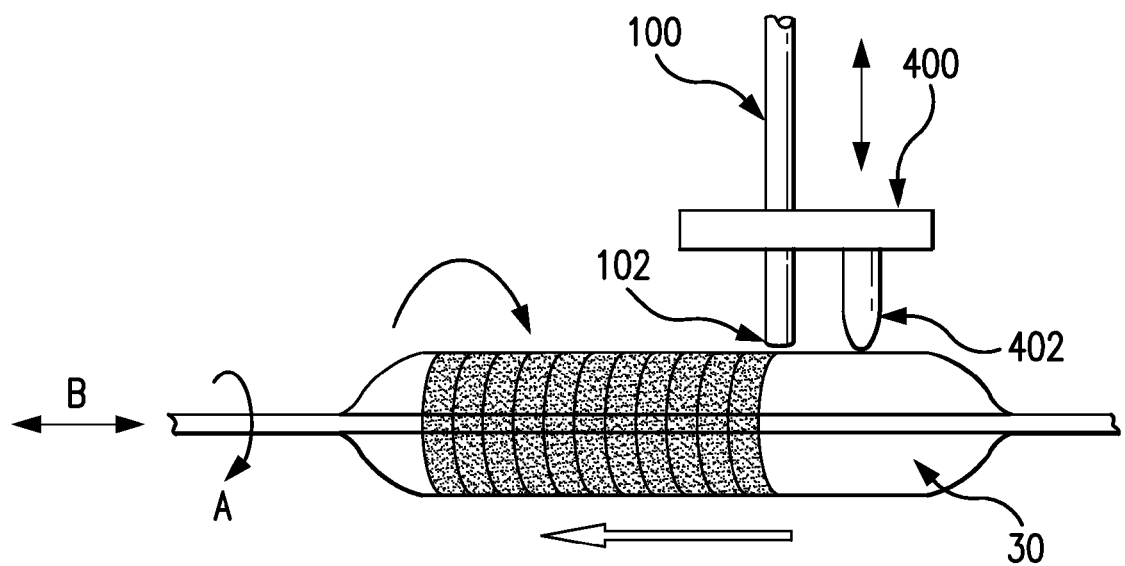
FIG. 4 is a schematic side view of an alternative tracking mechanism for an applicator outlet in accordance with the disclosed subject matter.

In an exemplary embodiment of the disclosed subject matter, illustrated in FIGS. 3-4, a tracking mechanism is provided to maintain a constant distance between the applicator outlet 102 and expandable member surface 30. Particularly, the tracking mechanism maintains the fixed distance by displacing the outlet of the applicator 100 to track the surface of the expandable member 30. As embodied herein, the applicator is mounted to a moveable base, wherein the base moves to track the surface of the expandable member. For example, in one embodiment of the tracking mechanism as shown in FIG. 3, a base 400 includes a movable portion 404, which can articulate about a pivot or hinge 405 relative to a fixed portion 406. As an alternative, and as depicted in FIG. 4, the base 400 can be free floating, such as on rails or a guide aligned perpendicular to the central axis of the expandable member, for displacement normal to the surface of the expandable member. Other moveable base configurations for a tracking mechanism can also be used.

Depending upon the type, size and configuration of the applicator, one or more components of the applicator can be mounted to the moveable base, whereas remaining components of the applicator and/or the fluid source can be mounted remotely in a fixed position. A suitable connection therefore is provided between the components mounted on the moveable base and those mounted remotely. At least the outlet of the applicator 100 is coupled to the base 400. For example, the outlet of applicator 100 can extend through an aperture formed in the base 400. Preferably, the outlet of the applicator 100 is rigidly attached or affixed to the base 400 to enable direct correlation between the degree or distance the base 400 is displaced and the distance the applicator outlet 102 is displaced.

As embodied herein, movement of the base is accomplished by direct physical contact with the surface of the expandable member. For example, a stylus 402 is positioned below the base, such as on the moveable portion 404 shown in FIG. 3 and the free floating base as shown in FIG. 4. Although only a single stylus is illustrated, it is to be understood that additional styluses can be provided. The stylus 402 can be fabricated of a durable, low friction material such as thermoplastic and thermoset polymers. Examples of which include, for purpose of illustration and not limitation, PEEK, polyethylene, polypropylene, polytetraflouroethylene, fluorinated ethylene propylene (FEP), poly(vinylidene fluoride), poly(tetraflouroethylene-co-ethylene), and nylons.

During the particular coating process, the stylus 402 is placed in contact with, and tracks the surface of the expandable member 30 during relative movement. As variations or non-uniformities of the expandable member surface are engaged by the stylus 402, the base 400 and thus applicator outlet 102 are displaced accordingly to maintain the fixed distance from the surface of the expandable member. The surface contour of the expandable member is thus conveyed by the stylus to the applicator outlet, resulting in a predictable and constant location of the applicator outlet relative to the surface of the expandable member. Accordingly, an expandable member having an asymmetrical shape or other variations in surface contour can be coated with a uniform coating.

The stylus 402 is preferably positioned proximate the applicator outlet 102 to avoid contact with the newly dispensed coating from the outlet. For example, the stylus 402 can be positioned laterally adjacent to or otherwise upstream of the applicator outlet 102 relative to the coating path, such as shown in FIG. 4 so as not to encounter fresh or wet coating of fluid. Furthermore, and as previously noted, the coating process allows for coating of select portions of the expandable member. For example, conventional expandable members generally have a cylindrical working length with tapered or stepped ends. If desired, a mechanism can be provided to disengage or deactivate the applicator as the stylus 402 approaches the tapered or stepped end or other select location along the working length of the expandable member 30. Similarly, the mechanism can operatively engage and raise the base 400 and/or deactivate the applicator 100 upon reaching the select location along the expandable member 30.

Based on this arrangement, the applicator outlet (e.g., spray nozzle, pipette, etc.) can be disposed a predetermined distance from the surface of the expandable member such that a controlled and uniform coating is applied over the desired length of the expandable member. Further, the predetermined arrangement between the applicator outlet and the stylus can be adjusted to vary the distance from the applicator outlet to the expandable member surface to accommodate various sizes of expandable members, as well as various sizes or types of applicators.

Additionally, and as previously noted, the tracking mechanism is capable of moving, e.g., translating and rotating about the expandable member's longitudinal axis. In some embodiments, the tracking mechanism can be configured to translate along a rail or similar support structure arranged generally in parallel to the longitudinal axis of the expandable member such that the tracking member can translate and rotate relative to the expandable member during the coating process.

The embodiments illustrated in FIGS. 3-4 depict a tracking mechanism having a stylus with a discrete point of contact with the expandable member 30. This configuration provides sufficient rigidity and support to displace the applicator outlet, while minimizing the surface area of the expandable member in contact with the stylus, thereby reducing friction and the risk of damage to the expandable member surface. If desired, however, multiple points of contact or a larger area of surface contact can be provided. Furthermore, and as previously noted, a lubricant or the like also can be used to inhibit or prevent frictional forces during operation, while the lubricant or the like is not transferred to the expandable member to disrupt the coating's functionality.

In accordance with another aspect of the disclosed subject matter, the tracking mechanism can be configured for displacement of the applicator outlet in a first direction and a second direction in a plane generally orthogonal to the longitudinal axis in which the expandable member is supported. This aspect is particularly beneficial for use with an expandable member having a distorted or asymmetric configuration along its longitudinal axis, such as a bowed or warped balloon. For example, an expandable member of significant length, such as a peripheral balloon, can tend to bow or warp and thus result in an asymmetric shape. Likewise, distorted configurations can result from the particular material properties used for the expandable member, as well as the various manufacturing processes performed e.g., blowing, stretching, shrinking, welding, etc.

Figure 5A:
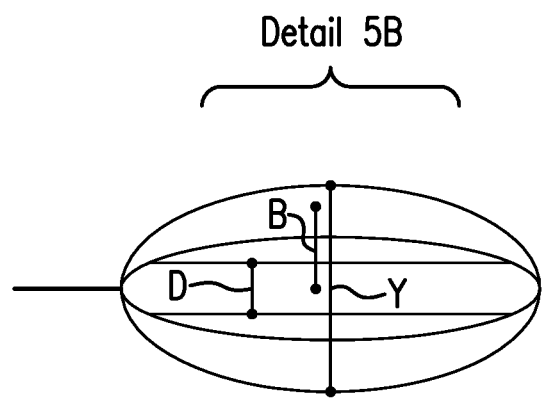
FIGS. 5A and 5B are a schematic side representation and an enlarged detail section, respectively, of an expandable member having a bowed configuration relative to a true symmetrical expandable member along a common longitudinal axis.
Figure 5B:
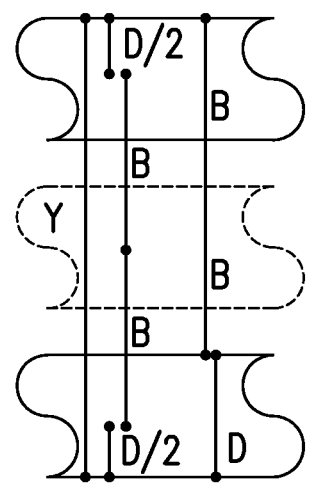

For purpose of explanation, one example of a quantitative measurement of the amount of asymmetry of an expandable member is depicted in FIGS. 5A and 5B. Particularly, FIG. 5A schematically depicts the distortion of a bowed balloon during rotation relative to a true symmetrical expandable member. FIG. 5B is an enlarged detail view of the schematic depiction of FIG. 5A to demonstrate certain relevant dimensions. As depicted, the amount of bowing of the expandable member is defined by the formula $B=(Y-D)/2$, wherein B is defined as the amount of bowing from a true longitudinal axis; D is defined as the diameter of the expandable member; and Y is defined as the distance from a surface of the expandable member with respect to the true longitudinal axis. Accordingly, for an expandable member, which is symmetrical about a central axis, the value of B is equal to zero.

Figure 6A:
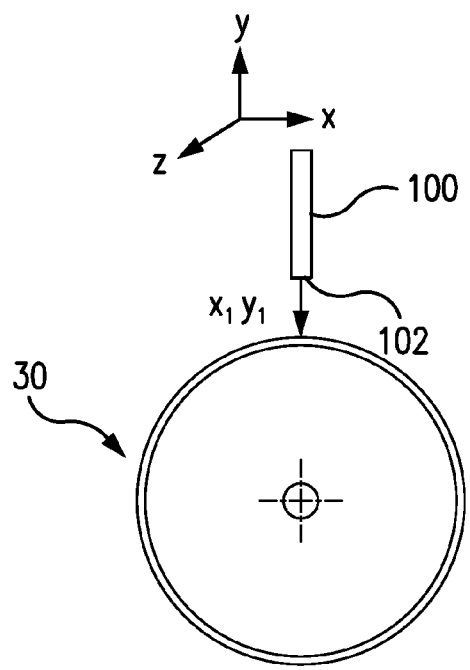
FIGS. 6A and 6B are schematic cross-sectional views of the spaced relationship between an applicator and an expandable member without and with a bowed configuration, respectively.
Figure 6B:
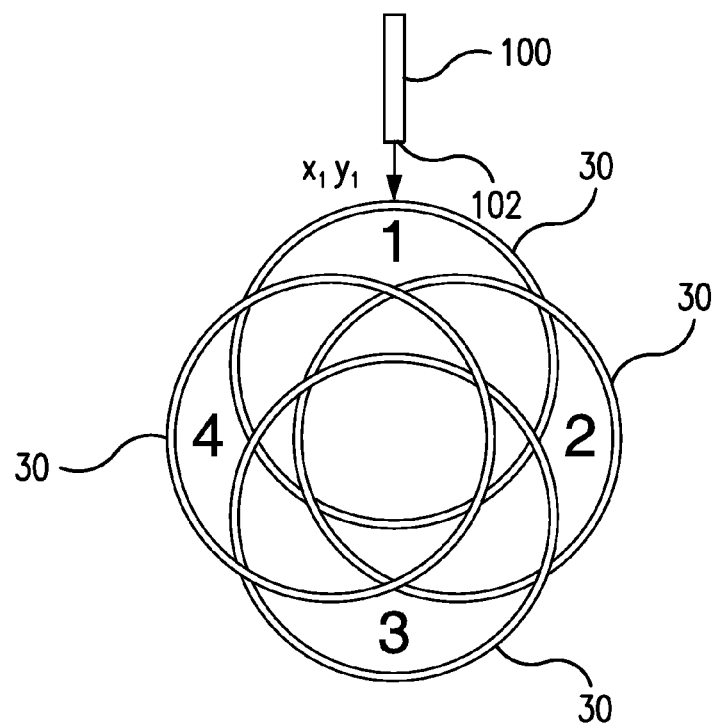

FIG. 6A illustrates a cross-sectional view of a true symmetrical expandable member. As shown in FIG. 6A, as the expandable member is rotated about its central axis, the distance from the applicator outlet to the top center of the balloon remains fixed at a constant position, indicated by coordinates $X_1 Y_1$. Accordingly, the applicator outlet can remain in a single and fixed position with the distance between the applicator and the expandable member remaining constant. By contrast, FIG. 6B depicts four (1-4) positions of rotation of an asymmetrical expandable member relative to an applicator outlet maintained in a fixed position. When the asymmetrical expandable member is rotated about its central axis, as illustrated in FIG. 6B, the distance between the fixed applicator outlet and the top center of the rotating expandable member (i.e., $X_1 Y_1$ in position 1) will vary in both the X axis and the Y axis—and thus result in a non-uniform coating. For purpose of illustration, the amount of bowing is exaggerated to demonstrate the amount of potential offset from the outlet of an applicator maintained at a fixed location.

Therefore, and as disclosed herein, a tracking mechanism is provided to maintain a fixed distance between the applicator outlet and the surface of the expandable member along both a first axis and a second axis in a plane generally orthogonal to the longitudinal axis in which the expandable member is supported. For example, the fixed distance can be maintained between the applicator outlet and the expandable member surface by employing a tracking mechanism for tracking the surface contour of the expandable member. The tracking mechanism is coupled to a floating applicator outlet such that the applicator outlet is configured for displacement along an X-axis and Y-axis in a plane disposed generally orthogonal to the longitudinal axis of the expandable member.

Figure 7:
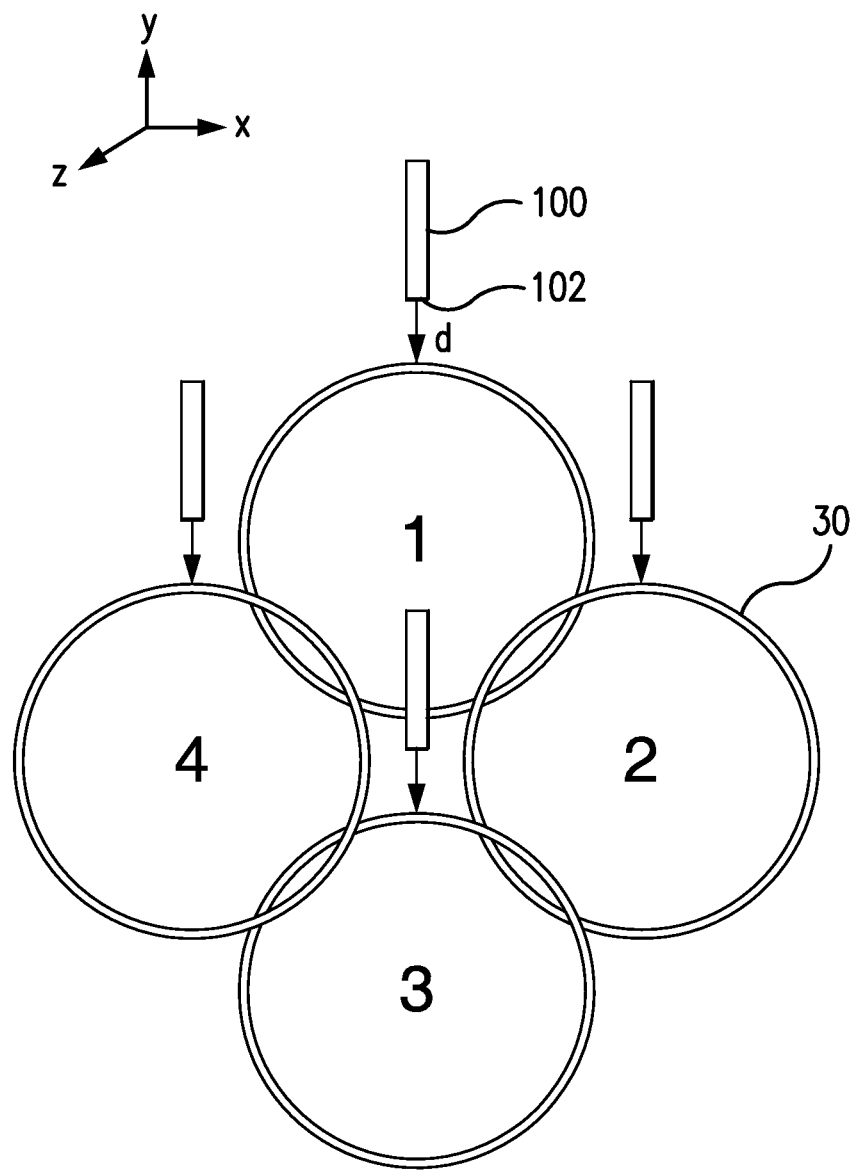
FIG. 7 is a schematic cross-sectional view demonstrating the fixed distance relationship between an applicator and an expandable member in accordance with the disclosed subject matter.

For purpose of illustration, FIG. 7 shows the applicator 100 configured for displacement in both the X-axis (e.g., horizontal as depicted) and Y-axis (e.g., vertical as depicted) directions such that a substantially fixed distance "d" can be maintained throughout each of positions 1-4 of relative movement throughout the coating process, and for any amount of asymmetry along the length of the expandable member.

Figure 8:
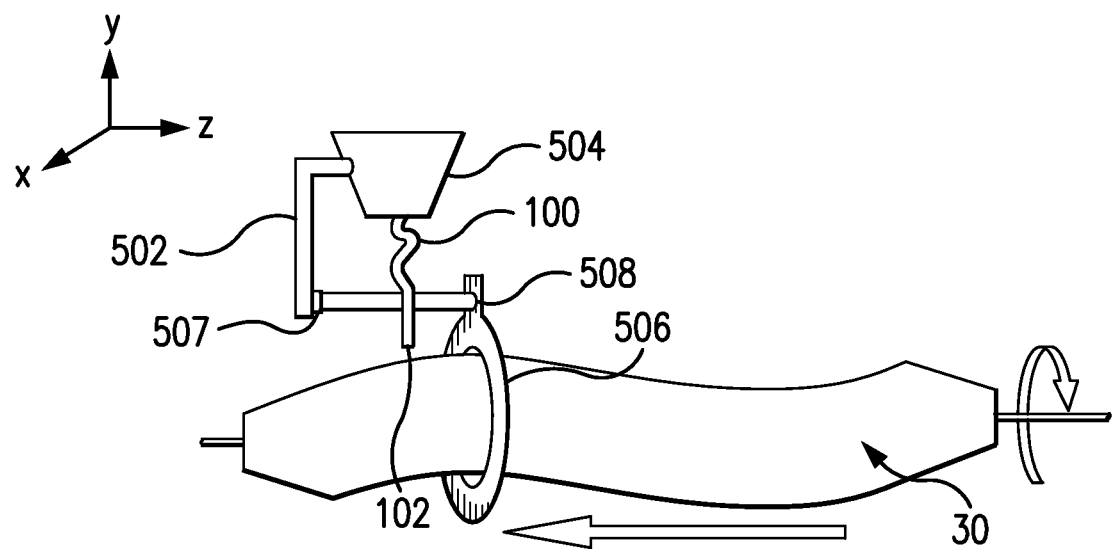
FIG. 8 is a schematic representation of an expandable member and an applicator with a tracking mechanism in accordance with the disclosed subject matter.

In an exemplary embodiment of the disclosed subject matter, illustrated in FIG. 8, a tracking mechanism 500 maintains the fixed distance by displacing the outlet 102 of the applicator to track the surface of the expandable member 30. The applicator outlet 102 includes a flexible connection with a fluid source via an applicator head 504 or the like as depicted in FIG. 8. In this embodiment, the applicator head 504 is secured to a retaining bracket 502 in a fixed location. A tip holder 508 extends from the retaining bracket 508, but is mounted for movement along the X-axis and Y-axis. As embodied herein, for purpose of illustration and not limitation, movement of the tip holder 508 is facilitated by a shuttle mechanism 507.

The tracking mechanism 500 also includes a guiding member 506 fixedly attached to a tip holder 508. The guiding member generally is sized and configured to generally surround the expandable member. For example, the guiding member 506 embodied herein is depicted as a circular hoop; however, a square frame or similar structure also can be used. Furthermore, the guiding member 506 can be adjustable in size and/or shape if desired. The outlet 102 of the applicator 100 is coupled to the tip holder 508. For example, the outlet 102 of applicator 100 can be secured to an edge of the tip holder 508, or can extend through an aperture formed in the tip holder 508. Preferably, the outlet of the applicator 100 is rigidly attached or affixed to the tip holder 508 to enable direct 1:1 correlation between the degree or distance the tip holder 508 is displaced and the applicator outlet 102 is displaced. The guiding member 506, tip holder 508, and applicator outlet 102 are thus in fixed relationship to each other and coupled to the shuttle mechanism 507.

Figure 9:
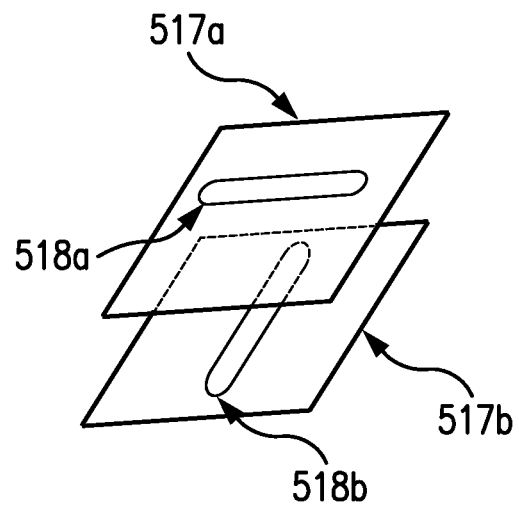
FIG. 9 is a schematic detail representation of shuttle mechanism in accordance with the disclosed subject matter.

For purpose of illustration and not limitation, the shuttle mechanism 507 can be a micro XY stage generally comprising two adjustable plates 517a, 517b. The first plate 517a has a slot or channel 518a orthogonal to a slot or channel 518b in the second plate 517b, as shown in FIG. 9. The first plate 517a is adjustable in a first direction, e.g., X-axis, and the second plate 517b is adjustable in a second direction, e.g., Y-axis. The two plates are arranged in a stacked or parallel manner with guide pin or the like extending through the slots 518a,b. For example, and with reference to FIG. 8, the plates of FIG. 9 would be arranged in an upright, vertical orientation, rather than the horizontal orientation as shown in FIG. 9. Displacement of the guiding member 506 due to engagement with the surface of the expandable member results in movement of the tip holder 508 as facilitated by the shuttle mechanism in a first direction (e.g., the X axis) along channel 518a and in a second direction (e.g., Y axis) along channel 518b. The shuttle mechanism can also include a spring or counterbalance to offset the weight of the tip holder 508, guiding member 506 and other components connected thereto.

As the guiding member 506 encounters variations in the surface contour of the expandable member 30, the variations are communicated via the guiding member 506 and tip holder 508 assembly to the shuttle mechanism 507. While FIG. 8 depicts one embodiment of the tracking mechanism in accordance with the disclosed subject matter, it is to be understood that other guide configurations can also be used. For example, a universal joint or other suitable hinge configuration can be used between the retaining bracket 502 and the tip holder 508 to allow movement of the applicator outlet generally along the X-axis and the Y-axis.

During operation of the particular coating process selected, as variations or non-uniformities of the expandable member surface are engaged by the guiding member 506, the variations in X and Y positioning are translated to the tip holder 508 and applicator outlet 102 accordingly through movement of the shuttle mechanism 507. As such, the applicator outlet 102 can be adjusted or moved as necessary in order to remain a constant distance from the expandable member 30 about the Y-axis, as well as remain positioned above the center of the expandable member with respect to the X-axis.

The applicator outlet 102, or at least a portion thereof, can be made of a non-rigid material to provide sufficient flexibility to allow displacement of the applicator outlet 102 about the X-axis and Y-axis. Additionally, or alternatively, the applicator outlet 102 can be constructed with a geometric structure, e.g., coil, corrugations, etc., that imparts flexibility to achieve the desired amount of displacement. This flexibility of the applicator outlet 102 allows for the guiding member 506, and tip holder 508 to be displaced with the shuttle mechanism 507.

Accordingly, as a bowed or otherwise non-cylindrical expandable member engages the tracking mechanism 500, the surface contour of the expandable member is conveyed to the applicator outlet 102, resulting in a predictable and constant location of the applicator outlet relative to the surface of the expandable member. Based on the known location of the expandable member, as well as the known relationship between the applicator (e.g., spray nozzle, pipette, etc.) and the tracking mechanism 500, a controlled and uniform coating can be applied over the desired length or area of the expandable member. Further, the arrangement between the applicator and the tracking mechanism 500 can be adjusted as so desired to accommodate various sizes of expandable members, as well as various sizes or types of applicators.

In an exemplary embodiment of the system and corresponding method of the disclosed subject matter, the translation of the expandable member 30 with respect to the guiding member 506 is a ratio of 1:1. Additionally, the expandable member can be inflated to an elevated pressure to offset or negate any compressive force resulting from the guiding member 506. Furthermore, and as previously noted, the tracking mechanism 500 can be configured with a counterbalance mechanism (not shown) to offset the gravitational and frictional forces between the guiding member 506 and the expandable member. Additionally, or alternatively, the guiding member 506 can be configured with a ball bearing assembly (not shown) or other low friction arrangements to further reduce any frictional forces between the guiding member 506 and the expandable member 30.

The guiding member 506 is preferably positioned relative the applicator outlet 102 to avoid contact with the newly dispensed fluid. For example, and as shown in FIG. 8, the guiding member 506 can be positioned in a location upstream of the applicator outlet 102 along the coating path so as not to encounter a fresh or wet coating of fluid. The guiding member 506 can be coated with or fabricated of a durable, low friction material such as thermoplastic and thermoset polymers. Examples of which include, for purpose of illustration and not limitation, Teflon, PEEK, polyethylene, polypropylene, polytetraflouroethylene, fluorinated ethylene propylene (FEP), poly(vinylidene fluoride), poly(tetraflouroethylene-co-ethylene), and nylons. Particularly, it is beneficial to reduce or minimize points of contact and frictional forces generated during the relative movement between the tracking mechanism and the expandable member.

If desired, a protective sheath can be provided to protect the coating during shipping and storage and/or during delivery of the coated expandable member through the body lumen. A variety of sheaths are known, including removable sheaths or balloon covers, retractable sheaths to be withdrawn prior to deployment of the balloon, and elastic sheaths that conform to the balloon upon expansion. Such elastic sheaths can be porous or include apertures along a portion thereof. In operation, the inflation of the expandable member causes the sheath to expand for release of the coating and/or therapeutic agent through the porous wall or apertures to the tissue of the arterial wall. For example, see U.S. Pat. No. 5,370,614 to Amundson et al., the disclosure of which is incorporated by reference in its entirety.

In accordance with in the disclosed subject matter, an endoprosthesis, e.g., stent, can be mounted on the expandable member. The type of stent that can be used includes, but is not limited to, bare metal stent, drug eluting stent, bioabsorbable stent, balloon-expandable stent, self-expanding stent, prohealing stent, and self-expanding vulnerable plaque implant. The expandable member can be coated independently of the stent or in conjunction with the stent coating process. The stent coating can contain the same or different therapeutic agents from the catheter or expandable member. However, the particular coating on the catheter or expandable member preferably has distinct release kinetics from the therapeutic coating on the stent. The coating applied to the expandable member can be allowed to dry prior to placement of the stent thereon.

Alternatively, the endoprosthesis can be positioned and/or crimped on to the expandable member before the coating is allowed to dry or cure past a "tacky" state. This would enable adhesion of the coating between the expandable member and the endoprosthesis. This process increases the retention of the prosthesis onto the expandable member (acting as an endoprosthesis retention enhancer) thus reducing the risk of dislodgement of the endoprosthesis during the torturous delivery through the vascular lumen.

While the disclosed subject matter is described herein in terms of certain preferred embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method of coating a balloon of a medical device, comprising:
providing a balloon having a longitudinal axis, the balloon being at least partially inflated;
providing an applicator in fluid communication with a fluid source, the applicator having at least one outlet for applying fluid therefrom;
positioning the applicator proximate a surface of the balloon;
substantially surrounding a circumference of the balloon with a frame of a tracking mechanism transverse to the longitudinal axis for discrete contact between the frame and the surface of the balloon, the applicator being operatively coupled within the frame;
establishing relative movement between the at least one outlet and the surface of the balloon along a coating path; and
maintaining a substantially fixed distance between the at least one outlet and the surface of the balloon during relative movement therebetween, wherein maintaining the substantially fixed distance includes displacing the at least one outlet in response to contact of the frame of the tracking mechanism with the surface of the balloon to track the surface of the balloon; and
applying fluid from the at least one outlet to form a coating of fluid on the surface of the balloon along the coating path.

2. The method of claim 1, wherein the balloon is supported along a longitudinal axis, and the outlet is configured for displacement in at least one direction in a plane orthogonal to the longitudinal axis.

3. The method of claim 2, wherein the outlet is configured for displacement along at least a first axis and a second axis in the plane.

4. The method of claim 1, wherein the balloon is at least partially inflated prior to dispensing fluid to the surface of the balloon.

5. The method of claim 1, wherein the relative movement includes rotation, translation, or a combination thereof, of at least one of the balloon and the at least one outlet.

6. The method of claim 5, wherein the balloon is rotated relative to the at least one outlet at a speed of between about 5 rpm and about 1000 rpm.

7. The method of claim 5, wherein the balloon is translated relative to the at least one outlet at a speed of between about 0.02 cm/sec and about 10 cm/sec.

8. A system for coating a balloon of a medical device, the system comprising:
a balloon at least partially inflated;
a support structure configured to support the balloon along a longitudinal axis;
an applicator in fluid communication with a fluid source, the applicator having at least one outlet for applying fluid of the fluid source therefrom, the applicator positioned with the outlet proximate a surface of the balloon supported by the support structure;
a drive assembly to establish relative movement between the outlet and the surface of the balloon to apply fluid on the surface of the balloon along a coating path; and
a tracking mechanism configured to maintain a substantially fixed distance between the outlet and the surface of the balloon during relative movement therebetween, wherein the tracking mechanism includes a frame to substantially surround a circumference of the balloon transverse to the longitudinal axis for discrete contact between the frame and the surface of the balloon, the applicator being operatively coupled with the frame whereby maintaining the substantially fixed distance includes displacing the outlet in response to contact of the frame of the tracking mechanism with the surface of the balloon to track the surface of the balloon.

9. The system of claim 8, wherein the tracking mechanism includes a shuttle mechanism for displacement of the frame.

10. The system of claim 9, wherein the shuttle mechanism is a micro XY stage.

11. The system of claim 8, wherein the outlet is configured for displacement in at least one direction in a plane orthogonal to the longitudinal axis.

12. The system of claim 11, wherein the outlet is configured for displacement along at least a first axis and a second axis in the plane orthogonal to the longitudinal axis.

13. The system of claim 8, wherein the outlet is rigidly coupled to the tracking mechanism.

14. The system of claim 8, wherein the applicator includes a flexible connection between the outlet and the fluid source.

15. The system of claim 8, wherein the substantially fixed distance is less than about 40 times a cross dimension of the outlet.

16. The system of claim 8, wherein the frame comprises at least one of a circular hoop or a square frame.

* * * * *